United States Patent
Zehnder et al.

(10) Patent No.: US 10,434,038 B2
(45) Date of Patent: Oct. 8, 2019

(54) SOLID PHOSPHONATE SALTS AS AN ADD-ON IN ENDODONTICS

(71) Applicant: smartodont GmbH, Zurich (CH)

(72) Inventors: Matthias Zehnder, Zurich (CH); Dirk Mohn, Zurich (CH)

(73) Assignee: SMARTODONT GMBH, Zurich (CH)

( * ) Notice: Subject to any disclaimer, the term of this patent is extended or adjusted under 35 U.S.C. 154(b) by 0 days.

(21) Appl. No.: 15/677,713

(22) Filed: Aug. 15, 2017

(65) Prior Publication Data
US 2018/0042821 A1 Feb. 15, 2018

(30) Foreign Application Priority Data
Aug. 15, 2016 (EP) .................................. 16184212

(51) Int. Cl.
*A61K 31/66* (2006.01)
*A61K 9/48* (2006.01)
*A61K 9/20* (2006.01)
*A61Q 11/00* (2006.01)
*A61K 6/00* (2006.01)
*A61K 9/70* (2006.01)
*A61K 31/662* (2006.01)

(52) U.S. Cl.
CPC .......... *A61K 6/0035* (2013.01); *A61K 6/0038* (2013.01); *A61K 9/70* (2013.01); *A61K 31/662* (2013.01)

(58) Field of Classification Search
CPC ....... C07F 9/3839; A61K 9/4858; A61K 9/20; A61K 33/40; A61K 31/662; A61Q 11/00

USPC ................... 514/141; 424/451, 464, 57, 665
See application file for complete search history.

(56) References Cited

U.S. PATENT DOCUMENTS

| | | | |
|---|---|---|---|
| 2003/0156980 A1 | 8/2003 | Fischer et al. | |
| 2007/0151044 A1* | 7/2007 | Cassier | A61K 8/042 8/405 |
| 2012/0211031 A1* | 8/2012 | Loeffler | C11D 3/378 134/25.2 |

FOREIGN PATENT DOCUMENTS

| | | |
|---|---|---|
| GB | 2095694 A | 10/1982 |
| WO | 03061506 A2 | 7/2003 |
| WO | 03101462 A2 | 11/2003 |
| WO | 2005123007 A1 | 12/2005 |

OTHER PUBLICATIONS

Lottanti, et al., "Effects of ethylenediaminetetraacetic, etidronic and peracetic acid irrigation on human root dentine and the smear layer," International Endodontic Journal, 2009 (9 pages).
(Continued)

*Primary Examiner* — Shengjun Wang
(74) *Attorney, Agent, or Firm* — Patent Law Works LLP (57) ABSTRACT

A phosphonate salt for use in a dental treatment, in particular in a root canal treatment, for the manufacture of a pharmaceutical preparation, in particular as decalcifying agent and a pharmaceutical preparation for use in the dental treatment comprising a phosphonate salt and/or a phosphonate salt and a hydroxide compound in solid form are provided. A method of producing a pharmaceutical preparation and a kit of parts for manufacturing a pharmaceutical preparation for use in the dental treatment are provided.

6 Claims, 4 Drawing Sheets

(56) References Cited

OTHER PUBLICATIONS

Kandaswamy et al., "Effects of various final irrigants on the shear bond strength of resin-based sealer to dentin," Journal of Conservative Dentistry, Jan.-Mar. 2011, vol. 14, Issue 1 (3 pages).
European Search Report, EP 16 18 4212, Nov. 11, 2016 (9 pages).

* cited by examiner

SOLID PHOSPHONATE SALTS AS AN ADD-ON IN ENDODONTICS

CROSS REFERENCE TO RELATED APPLICATIONS

The present application claims the right of priority under 35 U.S.C. § 119(b) of European Application No. 16184212.5, entitled "SOLID PHOSPHONATE SALTS AS AN ADD-ON IN ENDODONTICS," filed on Aug. 15, 2016, the entire content of which are incorporated herein by reference.

BACKGROUND

The present invention relates to phosphonate salts for use in a dental treatment for the manufacture of pharmaceutical preparations.

PRIOR ART

In dentistry, especially in the field of endodontics, i.e. root canal treatments, it is generally known that an infected root canal system harbors many species of bacteria, their toxins and their by-products as a consequence of pathological changes in the dental pulp. Current concepts in restorative dental therapy largely rely on mechanical treatment such as drilling of dental hard tissue. However, during the mechanical treatment of dental hard tissue a smear layer consisting of organic and inorganic tooth components that covers the root canal walls is produced. In order to facilitate the antimicrobial action of antiseptic agents, said smear layer needs to be removed. In addition, removal of the smear layer is further necessary in order to enable an optimal bonding of tooth-colored restorations or root-filling materials to dentin.

In recent years, experts in the field of dentistry and medicine have developed a variety of irrigants and disinfectants for dental procedures as well as methods for removing smear layers, buildup of debris and bacteria formed during the preparation of tooth surfaces in procedures such as root canal treatment, restoration, and the like.

Methods for disinfecting and removing a smear layer from prepared tooth surfaces which involve irrigating the tooth surface with a disinfectant solution containing doxycycline or tetracycline, a surfactant such as polysorbate and an organic acid such as citric acid are known from WO 03/061506 A1.

US 2003/0156980 A1 discloses methods for disinfecting and cleaning dental root canals using a viscous sodium hypochlorite (NaOCl) composition, for example a disinfectant comprising an aqueous sodium hypochlorite solution and a gelling agent such as fumed silica or carboxypolymethylene.

Chelating agents were introduced into endodontics as an aid for the preparation of narrow and calcified root canals, where a liquid solution of ethylenediaminetetraacetic acid (EDTA) was thought to chemically soften the root canal dentine and dissolve the smear layer as well as to increase dentine permeability. Current chemical agents to remove a smear layer therefore often comprise EDTA and organic acids such as citric acid. EDTA is frequently used in aqueous gels for root canal therapy because it is assumed that its chelating capacity reduces stress on nickel-titanium instruments used in the mechanical treatment of the root canal system. However, whereas agents based on EDTA are capable of removing the inorganic portion of the smear layer, an organic smear layer is often left intact in the root canal system.

It has been shown that this drawback can be overcome by using EDTA and for example citric acid in combination with an oxidizing agent such as sodium hypochlorite (NaOCl), since NaOCl is a very efficient agent to dissolve the organic smear layer components. At the same time, NaOCl is a strong antimicrobial agent. However, it has been found that both EDTA and citric acid strongly interact with oxidizing agents such as NaOCl and render the oxidizing agents ineffective by accelerating the degradation of the available hypochlorite anion $OCl^-$. On the other side, both EDTA and citric acid are known to act as calcium complexing agents and are thus particularly useful if intracanal medications are based on calcium hydroxide.

In order to overcome the above mentioned drawbacks, WO 2005/123007 discloses a pharmaceutical preparation for use in a dental treatment comprising an aqueous solution of a phosphonate such as 1-hydroxyethane-1,1'-diphosphonate (HEDP) as calcium complexing agent and a diluted NaOCl solution as oxidizing agent. It was found that phosphonates are ideal substances for dentin debridement during or after mechanical tooth preparation. Moreover, the high calcium binding capacity of phosphonates in combination with their reduced interaction with oxidizing agents that are used to dissolve organic dentin components are ideal features to quickly and thoroughly remove a smear layer. However, the mixing of aqueous irrigants is neither user-nor manufacturer-friendly, particularly because NaOCl solutions are inherently non-stable and premixed solutions of both NaOCl and HEDP require shipping and storage subject to specific requirements and conditions in each case.

A root canal treatment of an infected canal system is typically performed in two visits. Between these visits, a disinfectant is placed in the root canal system so as to destroy remaining microorganisms and prevent reinfection. Calcium hydroxide ($Ca(OH)_2$) is commonly used between treatment appointments due to it its antibacterial effect, attributed to the fact that hydroxyl ions are released over time and diffuse through dentine. Frequently, aqueous solutions of NaOCl are used to rinse root canals during and after mechanical debridement, while calcium hydroxide slurries are placed in the thus-cleaned root canal system to disinfect between two dental visits. Calcium hydroxide exerts its antibacterial effect in the root canal system as long as a high pH value is maintained. However, the use of $Ca(OH)_2$ placed as a disinfectant in the root canal system has certain drawbacks. For example, calcium hydroxide has a low solubility in water and consequently the onset of its disinfecting effect is slow. Moreover, it has to be removed before the canal is filled with an alloplastic material, which is cumbersome, since calcium hydroxide particles are hard to retrieve from the root canal system.

SUMMARY OF THE INVENTION

It is therefore an object of the present invention to overcome the disadvantages associated with e.g. the storage, manufacture or application of currently known pharmaceutical preparations for use in a root canal treatment.

This object is achieved by a phosphonate salt for use in a dental treatment with a pharmaceutical preparation as claimed in claim 1.

This object is further achieved by the pharmaceutical preparation according to claim 12 and the method of producing a pharmaceutical preparation according to claim 14, respectively.

Furthermore, this object is achieved by the kit of parts according to claim 15.

Further embodiments of the invention are laid down in the dependent claims.

Hence, a phosphonate salt for use in a dental treatment, in particular in a root canal treatment, for the manufacture of a pharmaceutical preparation is provided, in particular as decalcifying agent.

That is, the phosphonate salt can be used for the manufacture of a pharmaceutical preparation which can be used immediately.

Phosphonates are obtained from deprotonated organophosphorus compounds containing R—C—PO(OH)$_2$, R—C—PO(OH)(OR) or R—C—PO(OR)$_2$ groups, where R refers to an alkyl or aryl radical. A phosphonate salt corresponds to the chemical compound of a deprotonated organophosphorus compound and one or more positive ions, for example one or more positively charged metal ions.

The phosphonate salt used for the manufacture of the pharmaceutical preparation preferably corresponds to a solid, undissolved phosphonate salt compound which is pharmaceutically acceptable and/or pure. The manufactured pharmaceutical preparation preferably corresponds to a sterile pharmaceutical preparation which can readily be used in the root canal treatment.

The phosphonate salt is preferably a salt of (1-hydroxyethane)-1,1'-di-phosphonic acid. This compound is a bisphosphonate also known as the salt of HEDP or as etidronate. HEDP is sometimes also referred to as (1-hydroxyethylidene)-1,1'-di-phosphonic acid or as 1-hydroxyethan-1,1-diyl)bis(phosphonic acid).

The salt of (1-hydroxyethane)-1,1'-di-phosphonic acid is preferably tetrasodium (1-hydroxyethane)-1,1'-di-phosphonate. Said compound has the molecular formula Na$_4$HEDP and corresponds to a solid, water-soluble composition. Na$_4$HEDP is sometimes also referred to as tetrasodium (1-hydroxyethylidene)-1,1'-di-phosphonate.

However, instead of or in addition to using tetrasodium, it is also conceivable to use any other alkali metal ion such as potassium or lithium. For example, it is conceivable to use tetrapotassium (1-hydroxyethylidene)-1,1'-di-phosphonate or tetralithium (1-hydroxyethylidene)-1,1'-di-phosphonate or a heterometallic combination thereof.

It is preferred that the pharmaceutical preparation further comprises an aqueous solution and/or an alkaline agent, the alkaline agent preferably being an oxidant.

In a first aspect, it is preferred to provide the phosphonate salt in a dose, in particular as a tablet or a capsule or in a water-soluble polymer foil, preferably in a water-soluble polymer foil comprising polyvinyl alcohol.

That is to say, the phosphonate salt can be provided at a predetermined amount and for this purpose be pressed to a tablet or contained in a capsule or in a water-soluble foil. In the latter case, the phosphonate salt can be wrapped into a water-soluble polymer foil or film as it is known in the art. Such foils or films can be made from a polyvinyl alcohol composition such as a partially hydrolyzed polyvinyl alcohol or a partially acetalized polyvinyl alcohol or a copolymer with polyvinyl alcohol, for example. Said polymer foil or film will dissolve when placed in an aqueous environment, preferably in a non-heated aqueous environment.

The alkaline agent is preferably sodium hypochlorite, which is also an oxidant and has the molecular formula NaOCl. In particular, the sodium hypochlorite can be provided as an aqueous, oxidizing solution comprising between 0.1 to 10 weight percentage, preferably between 0.5 to 7 weight percentage, particularly preferably between 1 to 5 weight percentage of sodium hypochlorite with reference to the total weight of the aqueous, oxidizing solution. Instead of providing NaOCl as the aqueous, oxidizing solution, it is also conceivable to use an aqueous hydrogen peroxide (H$_2$O$_2$) solution.

In addition, instead of dissolving Na$_4$HEDP in an aqueous, oxidizing solution, it is also possible to dissolve Na$_4$HEDP in an aqueous solution. For example, the phosphonate salt can be used for the manufacture of a pharmaceutical preparation by dissolving Na$_4$HEDP in water or in a saline solution. Such a pharmaceutical preparation mainly has a decalcifying effect and is particularly useful as a rinsing solution when revitalizing a child's teeth.

The pharmaceutical preparation preferably comprises between 2 to 40 weight percentage, preferably between 5 to 20 weight percentage, particularly preferably between 8 to 10 weight percentage of tetrasodium (1-hydroxyethane)-1,1'-di-phosphonate with reference to the total weight of the pharmaceutical preparation.

In a preferred application of the pharmaceutical preparation, about 1 gram of Na$_4$HEDP is pressed as a tablet or contained in a tablet or a capsule or in a water-soluble polymer foil, respectively, and is dissolved in about 10 milliliter of an aqueous sodium hypochlorite solution, where the aqueous sodium hypochlorite solution is provided in concentrations between 1 and 5 weight percentage of sodium hypochlorite with reference to the total weight of the aqueous sodium hypochlorite solution. In another preferred application of the pharmaceutical preparation, two such tablets or capsules or pads of water-soluble polymer foil containing the 1 gram of Na$_4$HEDP are dissolved in about 20 milliliter of said aqueous sodium hypochlorite solution.

Hence, the use of a phosphonate for the manufacture of a pharmaceutical preparation as explained above has the advantages of being user- and manufacturer-friendly, since it allows the manufacture of the pharmaceutical preparation immediately before use. In particular, the salt of Na$_4$HEDP dissolves quickly in an aqueous environment and can thus be mixed with the irrigant of the dentist's choice, e.g. a sodium hypochlorite solution, immediately prior to the treatment. This simplifies handling and storage issues associated with commonly used premixed mixtures of, for example, Na$_4$EDTA and a sodium hypochlorite solution.

In addition, the tedious mixing of aqueous solutions and the shipping and storage of premixed solutions under specified conditions is omitted. Furthermore, there is no significant loss of available hypochlorite anion formed from the decomposition of Na$_4$HEDP mixed with a NaOCl solution over the course of e.g. one hour and hence, the use of an effective oxidizing agent throughout the endodontic treatment is enabled.

Moreover, the high calcium binding capacity of the phosphonate salt in combination with its reduced interaction with any oxidizing agents such as NaOCl that are used to dissolve organic dentin components enables a quick and thorough removal of a smear layer during and after the mechanical treatment of the root canal treatment.

In a second aspect, the phosphonate salt and the alkaline agent are provided in a dose, in particular as a tablet or a capsule or in a water-soluble polymer foil, preferably in a water-soluble polymer foil comprising polyvinyl alcohol as explained above.

Hence, it is preferred to provide these compounds combined in a single dose. However, it is also conceivable to provide the phosphonate salt in one such dose and the alkaline agent in another such dose, i.e. to provide these compounds in separate doses.

The alkaline agent is preferably a hydroxide compound in solid form, in particular an alkaline earth metal hydroxide compound in solid form, preferably solid calcium hydroxide.

For example, it is preferred to use solid calcium hydroxide, which has the chemical formula $Ca(OH)_2$. However, it is also conceivable to use other alkaline earth metal hydroxide compounds such as magnesium hydroxide ($Mg(OH)_2$) or strontium hydroxide ($Sr(OH)_2$).

The hydroxide compound used for the manufacture of the pharmaceutical preparation preferably corresponds to a solid, undissolved hydroxide compound which is pharmaceutically acceptable and/or pure. The manufactured pharmaceutical preparation preferably corresponds to a sterile pharmaceutical preparation which can readily be used in the root canal treatment.

The pharmaceutical preparation preferably comprises between 5 to 30 weight percentage, preferably about 10 weight percentage, of tetrasodium (1-hydroxyethane)-1,1'-di-phosphonate with reference to the total weight of tetrasodium (1-hydroxyethane)-1,1'-di-phosphonate and solid calcium hydroxide.

It is preferred that the aqueous solution is sterile water or an aqueous sodium chloride solution, preferably an aqueous sodium chloride solution comprising between 0.5 to 1.5 weight percentage of sodium chloride, particularly preferably about 0.9 weight percentage of sodium chloride with reference to the total volume of the aqueous sodium chloride solution. For example, a commercially available, sterile sodium chloride solution of 0.9 weight per volume of NaCl can be used.

In a preferred application of the pharmaceutical preparation, about 10 weight percentage of $Na_4HEDP$ is mixed with up to 90 weight percentage of solid $Ca(OH)_2$ with reference to the total mass of $Na_4HEDP$ and $Ca(OH)_2$. Said mixture is either provided in a dose as described above, for example as a capsule containing about 1 gram of said mixture, or provided in a container comprising for example about 100 grams of said mixture. In the former case, one dose is preferably added to about 0.5-2 milliliter of a sterile sodium chloride solution of 0.9 weight per volume of NaCl. In the latter case, a user removes about the same amount of said mixture from the container and adds it to about 0.5-2 milliliter of a sterile sodium chloride solution of 0.9 weight per volume of NaCl. The addition of $Ca(OH)_2$ to the sodium chloride solution results in a slurry preferably comprising between 40 to 80, preferably 33 to 66, weight percentage of $Ca(OH)_2$ powder, in particular about 50 to 60 weight percentage of $Ca(OH)_2$ powder and thus a maximum of 1 milliliter of liquid in the case of a 1 gram dose.

Hence, the use of a phosphonate and an alkaline agent such as a hydroxide compound for the manufacture of a pharmaceutical preparation as explained above has the advantages of being user- and manufacturer-friendly, since it allows the manufacture of the pharmaceutical preparation immediately before use. In particular, the salt of $Na_4HEDP$ dissolves quickly in an aqueous environment and can thus be mixed with the aqueous solution immediately prior to the treatment.

In particular, when $Na_4HEDP$ is mixed with solid calcium hydroxide in an aqueous environment, the resulting slurry has a higher pH value which increases faster as compared to commonly used calcium hydroxide in an aqueous environment. Hence, the present pharmaceutical preparation results in an earlier onset of the desired disinfecting effect. In addition, the binding capacity of $Na_4HEDP$ to the calcium cation $Ca^{2+}$ facilitates the removal of the calcium hydroxide slurry from the root canal before the canal is filled with an alloplastic material.

In a third aspect, a pharmaceutical preparation for use in a dental treatment, in particular in a root canal treatment, comprising a phosphonate salt, or a phosphonate salt and a hydroxide compound in solid form, is provided.

The phosphonate salt is preferably a salt of (1-hydroxyethane)-1,1'-di-phosphonic acid as described above, in particular it is tetrasodium (1-hydroxyethane)-1,1'-di-phosphonate. The hydroxide compound is preferably an alkaline earth metal hydroxide compound as described above, in particular it is solid calcium hydroxide.

The pharmaceutical preparation preferably comprises the phosphonate salt dissolved in an aqueous solution or in a saline solution as described above, e.g. dissolved in an aqueous, oxidizing solution comprising sodium hypochlorite. It is also preferred that the pharmaceutical preparation comprises the phosphonate salt and the hydroxide compound admixed to an aqueous or saline solution as described above, e.g. admixed to sterile water or an aqueous sodium chloride solution.

The tetrasodium (1-hydroxyethane)-1,1'-di-phosphoniate and/or the tetrasodium (1-hydroxyethane)-1,1'-di-phosphoniate and the solid calcium hydroxide are preferably provided in a capsule or in a water-soluble polymer foil, preferably in a water-soluble polymer foil comprising polyvinyl alcohol, as described above.

In a fourth aspect, a method of producing a pharmaceutical preparation for use in a dental treatment, in particular in a root canal treatment, is provided, said method comprises the step of adding a phosphonate salt, preferably a salt of (1-hydroxyethane)-1,1'-di-phosphonic acid, particularly preferably tetrasodium (1-hydroxyethane)-1,1'-di-phosphonate, and preferably an alkaline agent such as sodium hypochlorite or a hydroxide compound in solid form, to an aqueous solution. The hydroxide compound is preferably an alkaline earth metal hydroxide compound such as solid calcium hydroxide.

Said method enables the production of a pharmaceutical preparation for immediate use in a dental treatment.

As aqueous solution either water or a saline solution can be used, which aqueous solution may further comprise an alkaline and/or preferably oxidizing agent. For example, said method enables the production of a pharmaceutical preparation by adding tetrasodium (1-hydroxyethane)-1,1'-di-phosphonate to an aqueous solution comprising sodium hypochlorite, or by adding tetrasodium (1-hydroxyethane)-1,1'-di-phosphonate and solid calcium hydroxide to an aqueous solution such as sterile water or to a sodium chloride solution. However, instead of dissolving $Na_4HEDP$ in an aqueous, oxidizing solution, it is also conceivable to dissolve $Na_4HEDP$ in an aqueous solution only.

The phosphonate salt and/or the phosphonate salt and the alkaline agent are preferably comprised in a capsule or in a water-soluble polymer foil as described above. Hence, it is particularly preferred to dissolve a specified amount, for example about 1 gram of $Na_4HEDP$ comprised in a capsule or in a water-soluble polymer foil in about 10 milliliter of a sodium hypochlorite solution, where the sodium hypochlorite solution is provided in concentrations between 1 and 5 weight percentage of sodium hypochlorite with reference to the total weight of the sodium hypochlorite solution. It is also particularly preferred to add a specified amount, for example 1 gram, of Na$_4$HEDP and Ca(OH)$_2$ comprised in a capsule or in a water-soluble polymer foil to about 0.5-2 milliliter of sterile water or to about 0.5-2 milliliter of a sodium chloride solution, where the sodium chloride solution contains about 0.9 percentage of sodium chloride with reference to the total volume of the sodium chloride solution. In other words, it is preferred to form a slurry comprising about 50-60 weight percentage of Ca(OH)$_2$ powder and less than 1 milliliter of the aqueous solution if a 1 gram dose of Na$_4$HEDP and Ca(OH)$_2$ is added to about 1 milliliter of a solution.

In a fifth aspect, a kit of parts for manufacturing a pharmaceutical preparation for use in a dental treatment, in particular in a root canal treatment, is provided, which kit comprises, in a separate compartment, a phosphonate salt, preferably a salt of (1-hydroxyethane)-1,1'-di-phosphonic acid, particularly preferably tetrasodium (1-hydroxyethane)-1,1'-di-phosphonate, and instructions for the manufacture of the pharmaceutical preparation comprising the step of adding the phosphonate salt to an alkaline solution comprising an oxidizing agent, preferably to a sodium hypochlorite solution. Or the kits of parts for manufacturing the pharmaceutical preparation comprises, in a separate compartment, a phosphonate salt, preferably a salt of (1-hydroxyethane)-1, 1'-di-phosphonic acid, particularly preferably tetrasodium (1-hydroxyethane)-1,1'-di-phosphonate, and a hydroxide compound in solid form, preferably an alkaline earth metal hydroxide compound, particularly preferably solid calcium hydroxide, and instructions for the manufacture of the pharmaceutical preparation comprising the steps of adding the phosphonate salt and the hydroxide compound in solid form to an aqueous solution.

That is to say, the kit preferably comprises Na$_4$HEDP in a separate compartment as well as instructions for the manufacture of the pharmaceutical preparation comprising the step of adding Na$_4$HEDP to a sodium hypochlorite solution. Alternatively, the kit preferably comprises Na$_4$HEDP and solid Ca(OH)$_2$ in a separate compartment and instructions for the manufacture of the pharmaceutical preparation comprising the step of adding the Na$_4$HEDP and the solid Ca(OH)$_2$ to an aqueous solution such as a NaCl or NaOCl solution. Said instructions can be printed on the kit or can be comprised in the kit, preferably in another separate compartment.

The phosphonate salt and/or the phosphonate salt and the hydroxide compound are preferably each provided in a dose, in particular as a tablet or a capsule or in a water-soluble polymer foil, as described above.

It is preferred that the kit further comprises, in a separate compartment, a measuring device such as a beaker or a microcentrifuge tube to provide a predetermined amount of the alkaline solution and/or of the aqueous solution to the pharmaceutical composition, or that the kit further comprises, in a separate compartment, a mixing surface such as a glass surface on which a predetermined amount of the aqueous solution is mixed with the phosphonate salt and the hydroxide compound.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

As already mentioned above, sodium hypochlorite solutions are inherently non-stable. Their stability is generally dependent on the concentration, the temperature, the pH-value and the exposure to light of the sodium hypochlorite solution as well as to the concentration of impurities which catalyze the decomposition in the sodium hypochlorite solution. It has been found that a decomposition of sodium hypochlorite proceeds quicker as the concentration of the hypochlorite solution increases. Furthermore, it has been shown that the decomposition increases over time and that the decomposition is greater at higher temperatures.

Figure 1:
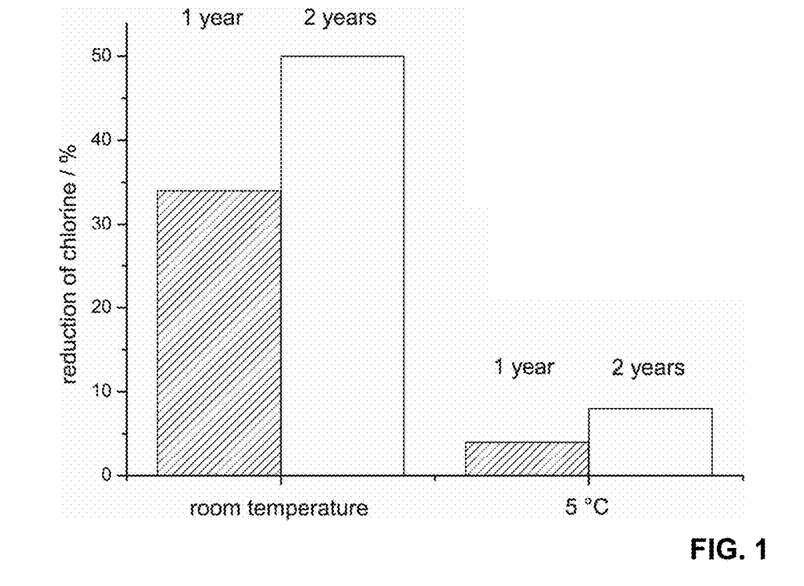
FIG. 1 shows the decomposition of a sodium hypochlorite solution comprising 5 weight percentage of sodium hypochlorite stabilized with a 0.5 molar sodium hydroxide solution stored for one year and for two years at two different temperature settings, i.e. at a room temperature of 23° C. and at 5° C.

As an illustration of the decomposition behavior of a sodium hypochlorite solution, FIG. 1 depicts the decomposition of a sodium hypochlorite solution comprising 5 weight percentage of sodium hypochlorite stabilized with a 0.5 molar sodium hydroxide solution stored for one year and for two years at room temperature of 23° C. and at 5° C. It follows from FIG. 1 that the sodium hypochlorite solution stored at room temperature decomposes to about 35 percentage and to about 50 percentage of available chlorine after one year of storage and two years of storage, respectively. However, the sodium hypochlorite solution stored at 5° C. decomposed to a much less degree, namely to about 5 percentage and to about 10 percentage of available chlorine after one year of storage and two years of storage, respectively. Hence, it is readily apparent from FIG. 1 that the stability of a sodium hypochlorite solution over time is greatly enhanced if it is stored at low temperatures. Besides, a sodium hypochlorite solution can generally be stabilized if a lye such as a sodium hydroxide (NaOH) solution is added.

Figure 2:
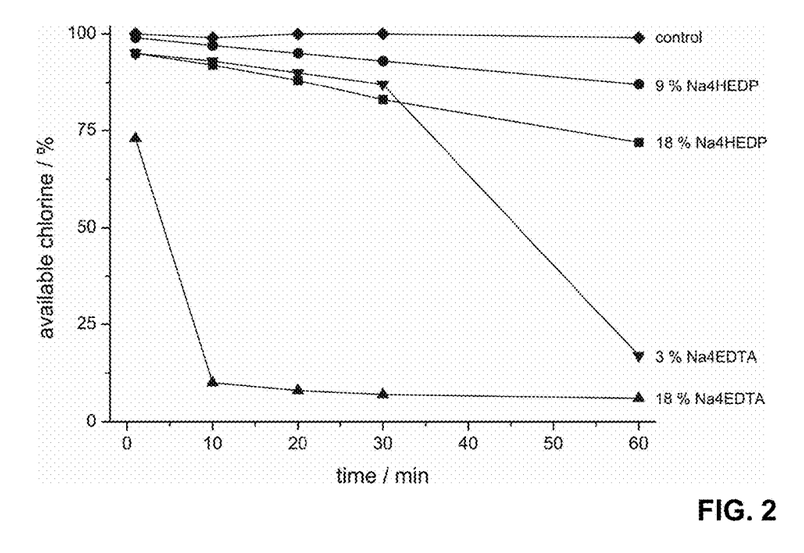
FIG. 2 shows the relative amount of chlorine from mixtures of a chelator and a sodium hypochlorite solution comprising 1 weight percentage of sodium hypochlorite compared to a pure NaOCl control solution during one hour. Four different mixtures, namely Na$_4$EDTA mixed with NaOCl and Na$_4$HEDP mixed with NaOCl at two different concentrations each, and a sodium hypochlorite solution are compared.
Figure 3:
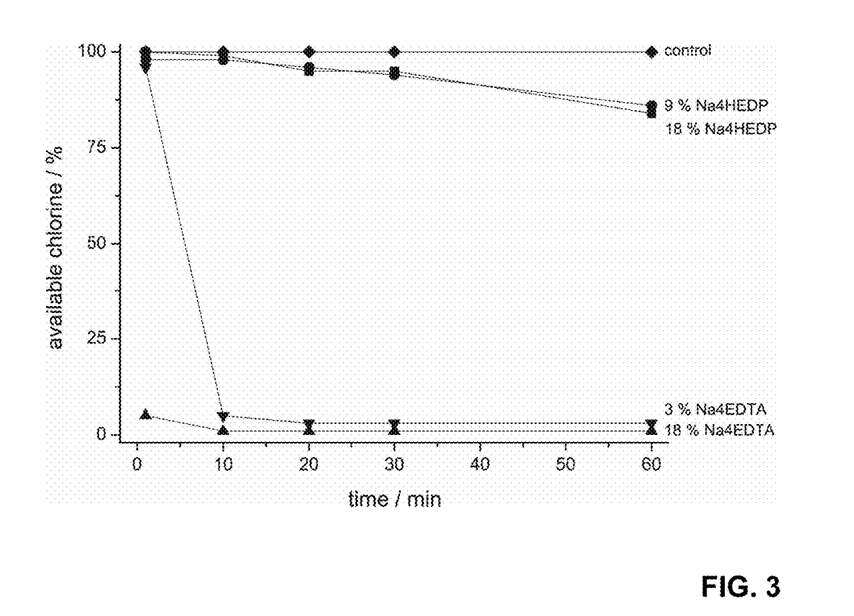
FIG. 3 shows the relative amount of chlorine from mixtures of a chelator and a sodium hypochlorite solution comprising 5 weight percentage of sodium hypochlorite compared to a pure NaOCl control solution during one hour. Four different mixtures, namely Na$_4$EDTA mixed with NaOCl and Na$_4$HEDP mixed with NaOCl at two different concentrations each, and a sodium hypochlorite solution are compared.

In FIGS. 2 and 3, the oxidizing effect of the hypochlorite anion over time is illustrated for the admixture of $Na_4HEDP$ compared to the commonly used admixture of $Na_4EDTA$ into a sodium hypochlorite solution comprising 1 and 5 weight percentage of sodium hypochlorite, respectively.

Although the chlorine reduction of the total solution is presented in FIG. 1 and the available chlorine is presented in FIGS. 2 and 3, respectively, the tissue dissolving capability is depending on the available hypochlorite $OCl^-$, which is directly related to chlorine. To measure the amount of hypochlorite, it has to be transferred by acidification to chlorine, which oxidizes potassium iodide to iodine. The latter is then titrated with a sodium thiosulfate solution.

In particular, FIG. 2 illustrates the amount of chlorine over time from mixtures of $Na_4HEDP$ as chelator and a sodium hypochlorite solution and of $Na_4EDTA$ as chelator and a sodium hypochlorite solution, respectively. In particular, the chlorine reduction from a 9 weight percentage and 18 weight percentage of $Na_4HEDP$ with reference to the total weight of the sodium hypochlorite solution as well as the chlorine reduction from a 3 weight percentage and 18 weight percentage of $Na_4EDTA$ with reference to the total weight of the sodium hypochlorite solution, respectively, was monitored over one hour, which is the normal duration of an endodontic treatment. The $Na_4HEDP$ and the $Na_4EDTA$ were each dissolved in a sodium hypochlorite solution comprising 1 weight percentage of sodium hypochlorite with reference to the total weight of the sodium hypochlorite solution.

The amount of chlorine over time was compared with a control solution of 1 weight percentage of pure sodium hypochlorite. In order to determine the amount of the available chlorine, aliquots of each solution (approximately 0.5 grams) were removed after 1 minute, 10 minutes, 20 minutes, 30 minutes and 60 minutes and assessed for their amount of available chlorine using a titration apparatus. Thereby, a 0.1 molar sodium thiosulfate solution was used as titrator. As is apparent from FIG. 2, the reduction of the chlorine from the decomposition of 9 weight percentage and 18 weight percentage of $Na_4HEDP$ mixed with a NaOCl solution comprising 1 weight percentage of NaOCl decays from almost 100 percentage to about 90 weight percentage and about 75 weight percentage, respectively. The chlorine reduction from the decomposition of a 3 weight percentage and 18 weight percentage of $Na_4EDTA$ mixed with a NaOCl solution comprising 1 weight percentage of NaOCl decays from about 95 weight percentage and 75 weight percentage, respectively, to below 25 weight percentage.

Hence, the admixture of $Na_4HEDP$ into the sodium hypochlorite solution maintained a high hypochlorite anion content, which is in clear contrast to low amount obtained from the commonly used admixture of $Na_4EDTA$ into the sodium hypochlorite solution. The latter caused a pronounced loss of available hypochlorite anions because EDTA strongly interacts with oxidizing agents such as NaOCl and thus renders the oxidizing agent ineffective. The immediate mixing procedure of $Na_4HEDP$ however does not cause any significant loss in available hypochlorite anions over the course of one hour and therefore enables the use of an effective oxidizing agent throughout the endodontic treatment.

In FIG. 3, the same measurements are performed using the same amounts of $Na_4HEDP$ and $Na_4EDTA$ as in FIG. 2, whereby these chelators are each admixed into a NaOCl solution comprising 5 weight percentage of NaOCl. As follows from FIG. 3, the reduction of the chlorine from the decomposition of $Na_4HEDP$ mixed with a NaOCl solution comprising 5 weight percentage of NaOCl is and remains much greater than the amount of the chlorine formed from the decomposition of $Na_4EDTA$ mixed with a NaOCl solution comprising 5 weight percentage of NaOCl. In fact, whereas the amount of the chlorine dropped by less than 25 percentage in the former case, a decrease to almost zero percentage occurred for the latter case over the course of one hour.

Besides, it has been shown that aqueous solutions of $Na_4HEDP$ are compatible with NaOCl irrigants and give the ability of a mild decalcification effect to these mixtures, which helps preventing the formation of a smear layer and debris accumulation during instrumentation.

As already mentioned, a disinfectant is placed in the root canal system so as to destroy remaining microorganisms and prevent reinfection. It is common to use calcium hydroxide $(Ca(OH)_2)$ due to it its antibacterial effect, which exerts its antibacterial effect as long as a high pH value is maintained.

Figure 4:
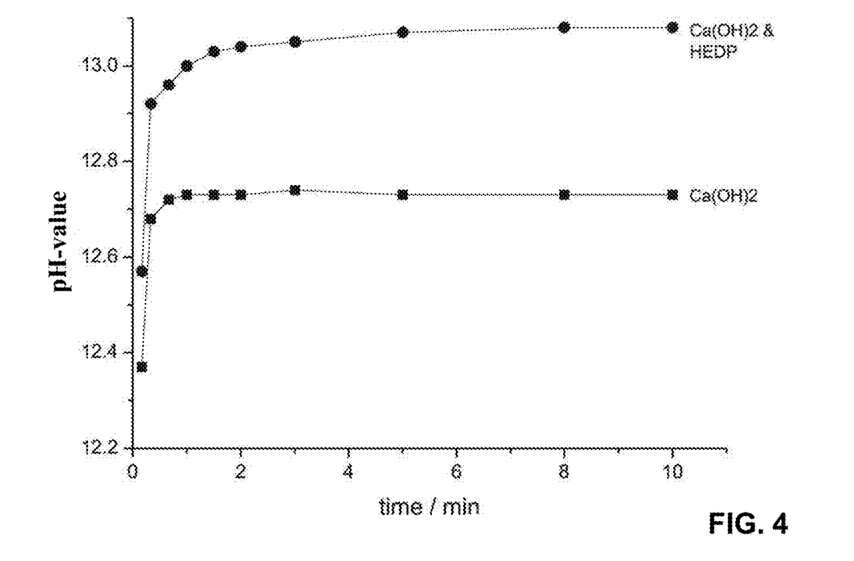
FIG. 4 shows the evolution of the pH-value of a solution of calcium hydroxide and Na$_4$HEDP in distilled water and the pH-value of a solution of calcium hydroxide in distilled water during 10 minutes.

FIG. 4 depicts the evolution of the pH-value over time determined for the admixture of $Na_4HEDP$ and calcium hydroxide in solid form and only calcium hydroxide in solid form, respectively, into distilled water. The solutions are prepared by mixing 1 gram of calcium hydroxide in solid form and 0.1 gram of $Na_4HEDP$ in a glass vial. 10 milliliter of distilled water was added, and the pH measurement was started immediately and continued for 10 minutes. As a control, the pH value of 1 gram pure calcium hydroxide dissolved in 10 milliliter of distilled water was recorded, too. As directly follows from FIG. 4, when particulate, i.e. solid $Na_4HEDP$ is mixed with the calcium hydroxide powder in an aqueous environment, the resulting slurry has a higher pH value which increases faster at the beginning as compared to the pH value obtained for a calcium hydroxide solution. This indicates that the $Na_4HEDP$ binds the calcium $Ca^{2+}$, thus liberating more hydroxyl ions. Consequently, the addition of $Na_4HEDP$ to calcium hydroxide can trigger an earlier onset of the desired disinfecting effect. In addition, the binding capacity of $Na_4HEDP$ to $Ca^{2+}$ makes it easier to remove the calcium hydroxide slurry from the root canal system before the canal is filled with an alloplastic material.

Figure 5:
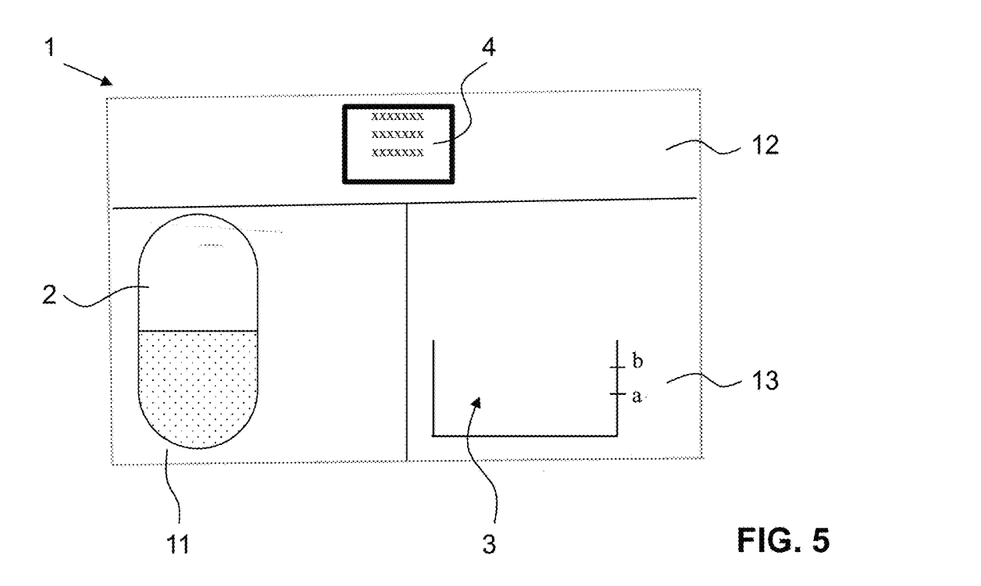
FIG. 5 shows a kit of parts according to a first embodiment.
Figure 6:
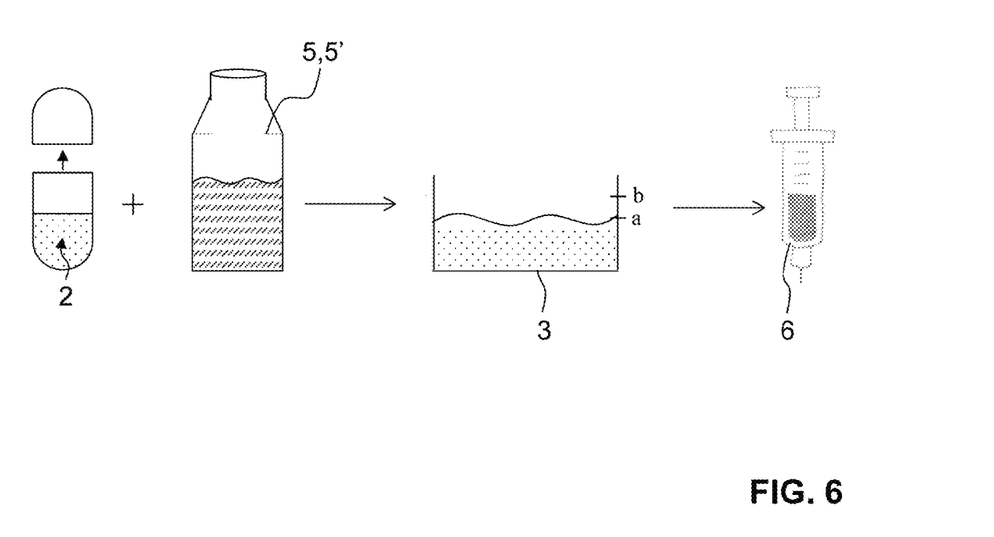
FIG. 6 shows a first illustration of the manufacture of a pharmaceutical preparation.
Figure 7:
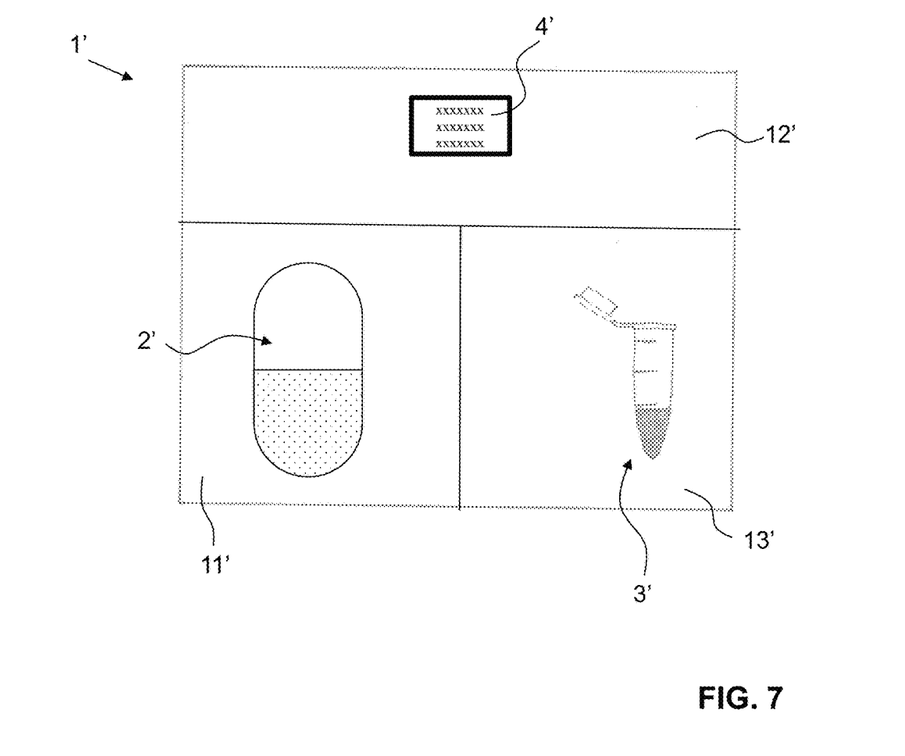
FIG. 7 shows a kit of parts according to a second embodiment.

FIGS. 5 and 7 show two embodiments of a kit of parts 1, 1' for manufacturing a pharmaceutical preparation for use in a root canal treatment. In particular, FIG. 5 shows a kit of part 1, which comprises a capsule 2 containing solid $Na_4HEDP$ in a first compartment 11 of the kit. Thereby, it is preferred to provide a container or the like containing a plurality of such capsules 2. In a second and third compartment 12, 13, the kit 1 comprises instructions 4 such as adding an aqueous, oxidizing solution to $Na_4HEDP$ for the manufacture of the pharmaceutical preparation and a measuring and mixing device 3 in the form of a mixing cup with a volume indication a, b for providing a specified amount of the aqueous, oxidizing solution. In the present example, the capsule contains about 1 gram of $Na_4HEDP$ and the instructions indicate to place either 10 milliliter or 20 milliliter of a sodium hypochlorite solution 5 comprising between 0.5 to 5 weight percentage of sodium hypochlorite with respect to the total mass of the sodium hypochlorite solution. As illustrated in FIG. 6, the capsule 2 containing the $Na_4HEDP$ can be opened or cracked at a predetermined breaking point in order to expose and release the $Na_4HEDP$ into the measuring cup. Once the $Na_4HEDP$ is dissolved in the sodium hypochlorite solution 5, the thus prepared pharmaceutical preparation is drawn up into a syringe 6 and can be discharged at a place of interest.

Figure 8:
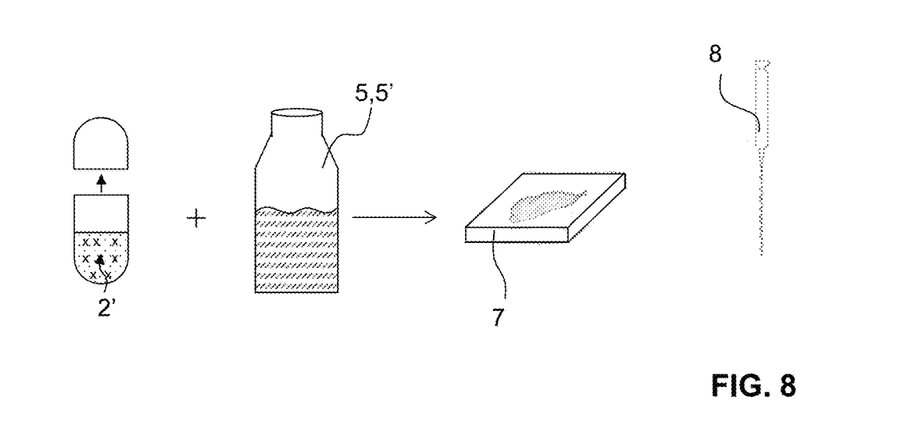
FIG. 8 shows a second illustration of the manufacture of a pharmaceutical preparation.

The kit of parts 1' shown in FIG. 7 comprises a capsule 2' containing solid Na₄HEDP and solid calcium hydroxide in a first compartment 11' of the kit 1'. Thereby, it is preferred to provide a container or the like containing a plurality of such capsules 2'. In a second and third compartment 12', 13', the kit 1' comprises instructions 4' such as adding water or a saline solution to Na₄HEDP and calcium hydroxide for the manufacture of the pharmaceutical preparation and a measuring and mixing device 3' in the form of a sealable microcentrifuge tube with a volume indication for providing a specified amount of water or of the saline solution. In the present example, the capsule contains about 1 gram of Na₄HEDP and Ca(OH)₂ and the instructions indicate to place about 0.5-2 milliliter of a sodium chloride solution 5' comprising 0.9 percentage of sodium chloride with respect to the total volume of the sodium chloride solution or of sterile water into the microcentrifuge tube 3'. As illustrated in FIG. 8, the capsule 2' containing the Na₄HEDP and the calcium hydroxide can be opened in order to expose and release the Na₄HEDP and the calcium hydroxide onto a glass plate 7. Once the Na₄HEDP and the calcium hydroxide are placed on the glass plate 7, the measured amount of the sodium chloride solution or of the sterile water is admixed to the Na₄HEDP and the calcium hydroxide. The thus prepared pharmaceutical preparation is of a slurry consistency and is placed on a point of interest by means of a Lentulo spiral 8.

It is to be noted that the kits of parts can comprise further compartments, for example a fourth compartment which comprises the glass plate or any further mixing or measuring devices or further components to be used in a root canal treatment. Instead of providing the instructions in a separate compartment in the kit, it is also possible to simply provide them within the kit or to imprint them onto the kit.

The invention claimed is:

1. A method of treating a patient suffering from an infected root canal, comprising administering an aqueous solution of a tetrasodium (1-hydroxyethane)-1.1'-di-phosphonate to the root canal, wherein the aqueous solution is manufactured immediately before its use from a pharmaceutical preparation comprising the tetrasodium (1-hydroxyethane)-1.1'-di-phosphonate in solid form and an aqueous solution of sodium hypochlorite.

2. The method of treating a patient suffering from an infected root canal according to claim 1, wherein the pharmaceutical preparation comprising the phosphonate salt is provided in a dose.

3. The method of treating a patient suffering from an infected root canal according to claim 1, wherein sodium hypochlorite is provided as an aqueous, oxidizing solution comprising between 0.1 to 10 weight percentage of sodium hypochlorite with reference to the total weight of the oxidizing solution.

4. The method of treating a patient suffering from an infected root canal according to claim 1, wherein the pharmaceutical preparation comprises between 2 to 40 weight percent of tetrasodium (1-hydroxyethane)-1,1'-di-phosphonate with reference to the total weight of the pharmaceutical preparation.

5. The method of treating a patient suffering from an infected root canal according to claim 2, wherein sodium hypochlorite is provided as an aqueous, oxidizing solution comprising between 0.1 to 10 weight percentage of sodium hypochlorite with reference to the total weight of the oxidizing solution.

6. The method of treating a patient suffering from an infected root canal according to claim 2, wherein the pharmaceutical preparation comprises between 2 to 40 weight percent of tetrasodium (1-hydroxyethane)-1,1'-di-phosphonate with reference to the total weight of the pharmaceutical preparation.

* * * * *